United States Patent [19]

Yamada

[11] Patent Number: 4,837,159
[45] Date of Patent: Jun. 6, 1989

[54] METHOD AND APPARATUS FOR EFFECTING IMMUNOLOGICAL ANALYSIS

[75] Inventor: Takashi Yamada, Sagamihara, Japan

[73] Assignee: Olympus Optical Co., Ltd., Sagamihara, Japan

[21] Appl. No.: 776,889

[22] Filed: Sep. 17, 1985

[30] Foreign Application Priority Data

Sep. 21, 1984 [JP] Japan ............................ 59-198054

[51] Int. Cl.⁴ ................ G01N 33/531; G01N 33/534; G01N 21/05
[52] U.S. Cl. ...................................... 436/45; 422/64; 422/67; 436/43
[58] Field of Search .................. 436/45, 43; 422/64, 422/67; 435/299, 300

[56] References Cited

U.S. PATENT DOCUMENTS

| Re. 31,149 | 2/1983 | Ginsberg et al. | 422/64 |
|---|---|---|---|
| 3,592,605 | 7/1971 | Noma et al. | 422/64 |
| 3,617,222 | 11/1971 | Matte | 422/64 |
| 3,644,095 | 2/1972 | Netheler et al. | 422/65 |
| 3,764,268 | 10/1973 | Kosowsky et al. | 422/64 |
| 3,917,455 | 11/1975 | Bak et al. | 422/64 |
| 3,932,131 | 1/1976 | Rolfo-Fontana | 436/45 |
| 4,200,607 | 4/1980 | Suzuki | 422/64 |
| 4,265,855 | 5/1981 | Mandle et al. | 422/65 |
| 4,451,433 | 5/1984 | Yamashita et al. | 422/67 |
| 4,457,893 | 7/1984 | Takekawa | 422/64 |
| 4,512,852 | 4/1985 | Tsuboshima et al. | 422/64 |
| 4,539,296 | 9/1985 | Manabe | 436/43 |

FOREIGN PATENT DOCUMENTS 0161864 9/1983 Japan ................................ 436/45

Primary Examiner—Barry S. Richman
Assistant Examiner—Timothy M. McMahon
Attorney, Agent, or Firm—Arnold, White & Durkee

[57] ABSTRACT

An automatic chemical analyzer for measuring given substances in samples in accordance with an enzyme-immuno-assay includes a turntable rotated intermittently at a constant pitch and holding a number of reaction tubes arranged equidistantly along a periphery of the turnable to define a circular reaction line; a carrier supply device for supplying carriers into reaction vessels one by one at a given position in the reaction line, said carrier having given antibody or antigen fixed thereto; a sample delivery device for pouring given amounts of samples into reaction vessels at a given position in the reaction line; a washing device for washing reaction vessels and carriers contained therein to effect B-F separation; a color reagent delivery device for pouring given amounts of a color reagent into reaction vessels to form test liquids; a colorimeter for photometering the test liquids; a carrier discharge device for removing carriers out of reaction vessels; and a control device for controlling on and off operation of said washing device such that different reaction time periods for various test items can be set.

16 Claims, 8 Drawing Sheets

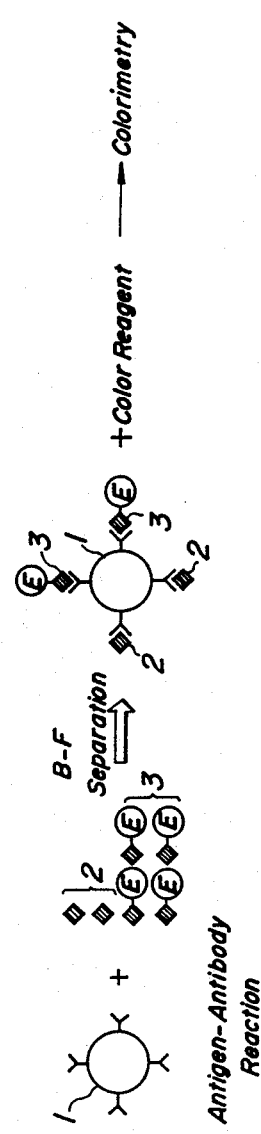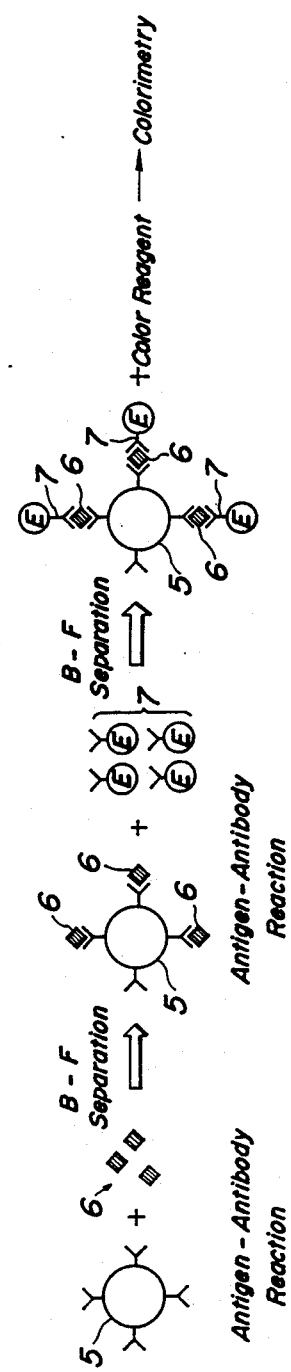

FIG_7A
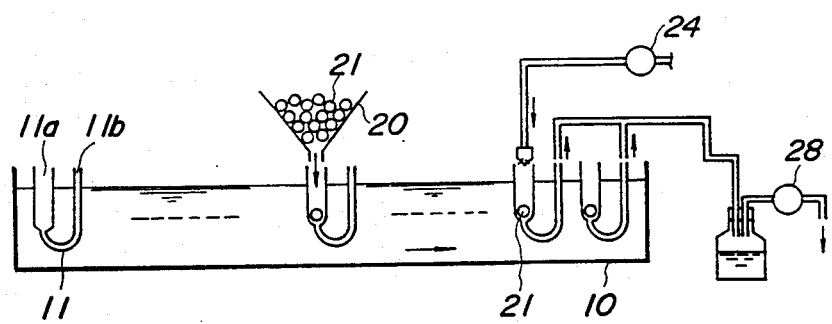
FIG.7B
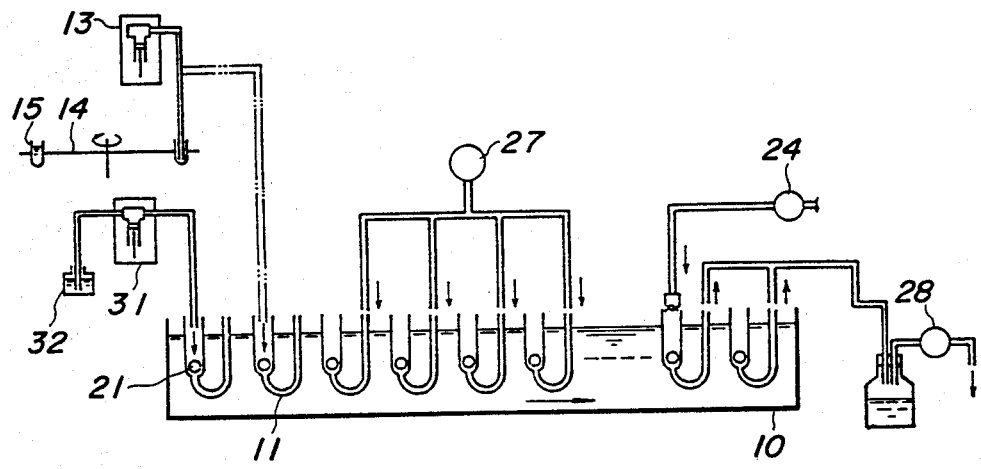
FIG.7C
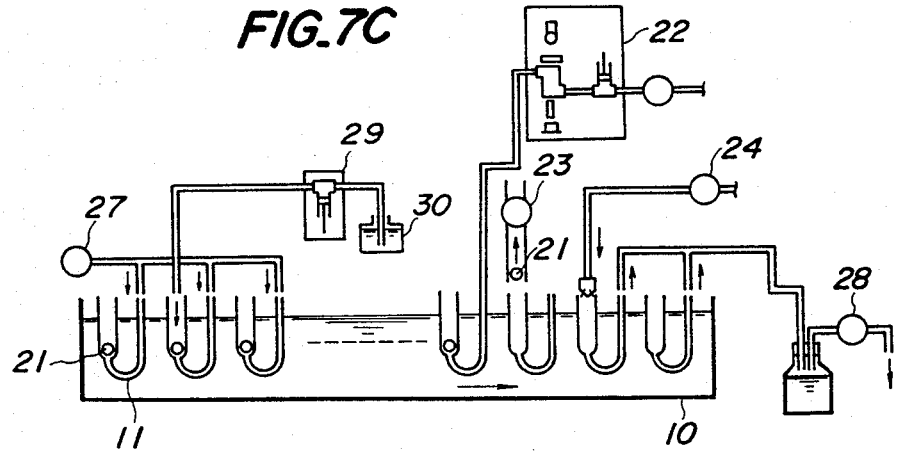

METHOD AND APPARATUS FOR EFFECTING IMMUNOLOGICAL ANALYSIS

BACKGROUND OF THE INVENTION

1. Field of the Invention

The present invention relates to a method and apparatus for effecting an immunological analysis.

2. Related Art Statement

Nowadays, due to the progress in medical treatment, very small amounts of biological substances in samples can be analyzed and this contributes to early diagnosis for various diseases. For instance, malignant tumors such as α-fetoprotein and carcinoembryonic antigen, diseases resulting in abnormal secretions of hormones such as insulin and thyroxine, and immunological diseases such as immunoglobulin can be diagnosed in early stages, and monitoring after treatments for these diseases can be carried out reliably. Moreover, the measurement of incomplete antigens, i.e. low molecular hapten of medical substances, contributes to make a plan of medication.

Many biological substances are analyzed in an immunological manner by utilizing the antigen-antibody reaction, and various methods for effecting the immunological analysis have been developed. For instance, existence or non-existence of agglutinated clots of antigen-antibody compound formed by the antigen-antibody reaction is detected by agglutination method, sedimentary method, nephelometry method, etc. to analyze desired biological substances. However, in the known methods, since the sensitivity is low, a large amount of antigen-antibody compound is required and only qualitative analyses or quasi-quantitative analyses can be performed. In order to avoid such a drawback, there have been further proposed the following methods. In one of the known methods, antigen or antibody is bound with carbon or synthetic resin fine particles which are then subjected to the antigen-antibody reaction with the biological substances to be analyzed, and the substances are detected by means of the agglutination method or nephelometry method, In another known method, antigen-antibody compounds are detected at a high sensitivity by using antigen or antibody marked with labeling material such as radioisotope, fluorescent material, luminescent material and enzyme. However, since the former method is inferior to the latter method in sensitivity, recently the latter method using the high sensitivity labeling substance has been predominantly adopted.

The analytic methods using the markers are classified into radio-immuno-assay using radioisotope tracers, fluorescent-immuno-assay using fluorescent labeling material, and enzyme-immuno-assay using enzyme markers. Among these methods, the enzyme-immuno-assay has been particularly developed because it does not require special installation and measuring techniques and can be performed easily by using commonly developed colorimeters. The enzyme-immuno-assay is further classified into homogeneous enzyme-immuno-assay and heterogeneous enzyme-immuno-assay. In the homogeneous analysis, a variation in the activity of labeling enzyme due to existence or non-existence of the immunological reaction is directly measured to detect substances to be analyzed. In the heterogeneous analysis, use is made of insoluble carriers such as glass beads or synthetic resin particles on which antigen or antibody has been fixed. Enzyme labeled antigen or antibody bound with the antibody or antigen fixed on the carriers and free enzyme-labeled antigen or antibody not bound with the antibody or antigen on the carriers are separated from each other by washing treatment, and then an activity of labeling enzyme is detected to measure a quantity of substances to be analyzed. Hereinbelow, the process for separating the bound antigen or antibody and the free antigen or antibody from each other is termed as B-F separation for the sake of simplicity. Although the homogeneous analysis can be performed by simple processes, it can analyze only the low molecular hapten such as medical substances, but cannot analyze high molecular biological substances. Contrary to this, in the heterogeneous analysis, although the washing process is required for effecting the B-F separation, it can be applied to any kinds of low and high molecular substances. Therefore, recently the heterogeneous enzyme-immuno-assay has been generally adopted.

In the heterogeneous enzyme-immuno-assay, there have been developed a competitive method and a sandwich method. Now these methods will be explained with reference to the drawings.

FIG. 1 illustrates successive steps of the competitive method. Given antigen or antibody which reacts with antibody or antigen substances 2 of a sample has been previously fixed to an outer surface of an insoluble carrier 1. At first, the antigen-antibody reaction is carried out between the antigen or antibody fixed onto the carrier 1 and the antibody or antigen 2 in the sample as well as a labeled reagent 3 which has been prepared by labeling substances same as the substances 2 to be analyzed with enzyme marker. Then, a washing process is carried out to effect the B-F separation between the substance 2 and labeled reagent 3 bound with the carrier 1 due to the antigen-antibody reaction and free substances 2 and reagent 3 which are not bound with the carrier 1. Next, a color reagent which selectively reacts with the labeling enzyme is added and a reaction liquid is colorimetered to detect the enzyme activity of the labeling enzyme.

FIG. 2 shows successive steps of the sandwich method in which use is made of an insoluble carrier 5 having antibody or antigen fixed thereto which is reactive with antigen or antibody substances in a sample 6 to be tested. At first, the carrier 5 and the sample 6 are mixed to effect the antigen-antibody reaction between the substances 6 in the sample and the antibody or antigen fixed to the carrier 5. Then, the B-F separation is carried out by means of the washing step. Next, a labeled reagent 7 is added to effect the antigen-antibody reaction. The labeled reagent is prepared by marking with enzyme substance selectively reacting with the substance 6 to be analyzed. Then, after the B-F separation is effected again, a color reagent reacting with the labeling enzyme in the labeled reagent 7 is added and a test liquid thus obtained is colorimetered to detect the activity of the labeling enzyme.

As exlained above, in the heterogeneous immuno-assay the B-F separation has to be carried out once in the competitive method and twice in the sandwich method during the analysis for respective sample, and further if a reaction vessel for effecting the antigen-antibody reaction is used repeatedly there must be further provided a step for washing the reaction vessel after the end of analysis for a sample but before the start of analysis for another sample. In case of automating, the enzyme-immuno-assay requires at least two washing steps including the B-F separation, and separate washing devices may be provided at different positions. However, in this case an automatic analyzer is liable to be large in size, complex in construction and expensive in cost. This disadvantage will also appear in automatic analyzers effecting radio-immuno-assay and fluorescent-immuno-assay. Moreover, in the automatic analyzers mentioned above, it is very rare that the measurement is performed for only one test item, and usually the measurement for multiple test items is effected. However, in the measurement for multiple test items, it is very difficult to manufacture reagents by means of which reaction time periods of the immunological reaction and the enzyme reaction in various test items can be made constant.

In order to adapt the analyzer to various reaction times corresponding to respective test items, usually a step period for transporting the reaction vessel has been varied, but this method has the drawbacks such that a control of the apparatus becomes complicated and the apparatus becomes expensive.

SUMMARY OF THE INVENTION

The present invention has for its object to eliminate the drawbacks mentioned above and to provide a method and an apparatus for effecting an immunological analysis which can effectively perform the measurement for multiple test items each having different reaction times.

According to the invention, a method of automatically analyzing given substances in samples in an immunological manner comprises transporting a number of reaction vessels containing carriers onto which given antibody or antigen has been fixed along an endless reaction line; delivering samples and labeled reagents into the reaction vessels to initiate antigen-antibody reaction; effecting a B-F separation by separating antigen or antibody bound with the carriers and free antigen or antibody from each other by means of a washing device; measuring the given substances in the samples with the aid of labeling substances of the labeled reagent; and discharging the carriers out of the reaction line; the improvement comprising controlling the washing device in a manner such that washing is effected when a reaction time period required for said antigen-antibody reaction is elapsed, said reaction time being set to a sum of a minimum time period and a multiple integer of a basic time period, wherein said minimum time period is equal to a period during which said reaction vessel moves from a reaction start position to a position at which the washing device is provided, and said basic time period is equal to a period during which said reaction vessel is rotated by one revolution.

According to the invention, an automatic analyzer for analyzing given substances in samples in an immunological manner comprises:

means for transporting a number of reaction vessels along an endless reaction line;

means for supplying carriers into reaction vessels at a given position in the reaction line, said carriers having given antibody or antigen fixed thereto;

means for supplying given amounts of samples into the reaction vessels at a given position of the reaction line;

means for delivering given amounts of a labeled reagent into the reaction vessels at a given position in the reaction line;

means for washing the reaction vessels and carriers to effect a B-F separation for separating antigen or antibody bound with the carriers and free antigen or antibody;

means for measuring the given substances in the samples with the aid of labeling substances of the labeled reagent;

means for discharging the carrier from the reaction vessel; and means for controlling on and off operation of said washing means in accordance with a reaction time period of a currently measured sample.

BRIEF DESCRIPTION OF THE DRAWINGS

FIG. 1 is a schematic view showing successive steps of a known competitive method;

FIG. 2 is a schematic view illustrating successive steps of a known sandwich method;

FIGS. 7A to 7C are schematic views illustrating an operation of the automatic analyzer shown in FIG. 6.

DESCRIPTION OF THE PREFERRED EMBODIMENTS

Figure 3:
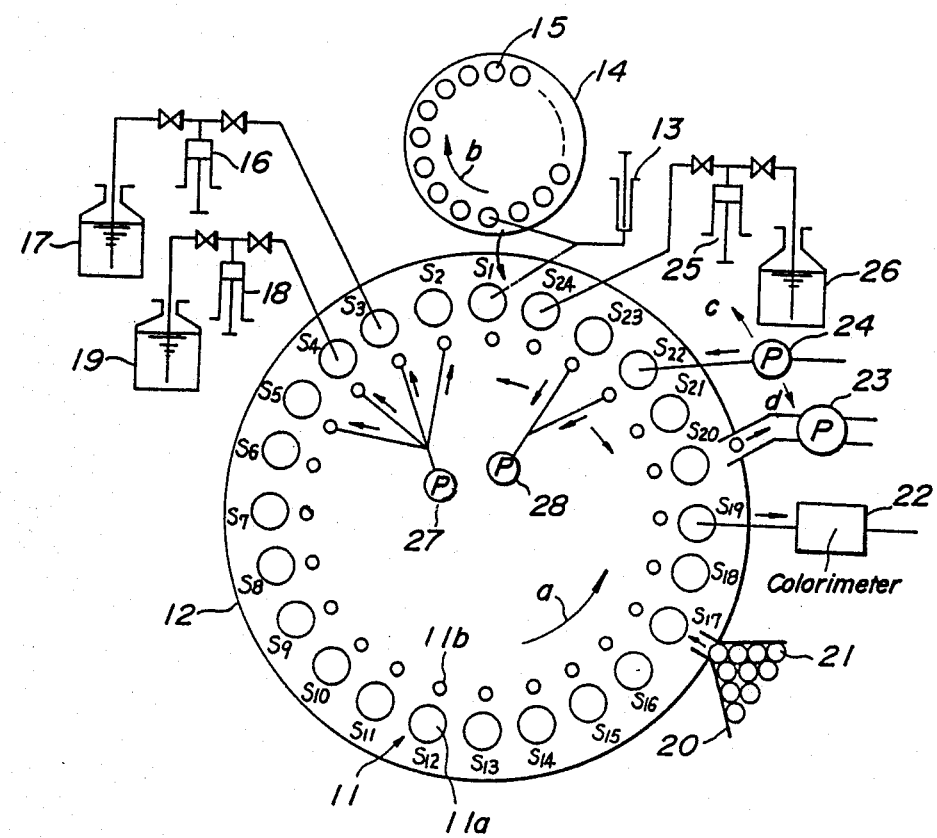
FIG. 3 is a schematic view depicting an embodiment of the enzyme-immuno-assay automatic analyzer according to the invention.

FIG. 3 is a schematic view showing an embodiment of the enzyme-immuno-assay automatic analyzer according to the invention which performs the sandwich method explained above with reference to FIG. 2. In the present embodiment, there is provided a single reaction line. As a reaction vessel, use is made of a U-shaped tube 11 having large and small mouth portions 11a and 11b. On a turntable 12 are arranged equidistantly twenty four U-shaped tubes 11 along a periphery of the turntable. The turntable 12 is intermittently rotated in a direction shown by an arrow a at a given period of, for example, 15 seconds while the U-shaped tubes 11 are dipped into a thermostat 10 (see FIG. 4). Positions at which the U-shaped tubes 11 are stopped due to the stepwise rotation of the turntable 12 are denoted as $S_1$ to $S_{24}$. In the present embodiment, into a U-shaped tube 11 positioned at $S_1$ is delivered a sample from a sample cup 15 which is situated just at a sample sucking position of a sampler 14 by means of a sample delivery device 13. The sampler 14 holds twenty four sample cups 15 arranged equidistantly along a disc which is rotated intermittently in a direction b in synchronism with the rotation of the turntable 12. In a U-shaped tube 11 in $S_3$ is selectively delivered an enzyme reagent 17 corresponding to substances in samples to be tested, by means of a reagent delivery device 16. In a U-shaped tube 11 situating at $S_4$ is poured a color reagent 19 with the aid of a reagent delivery device 18. Into a U-shaped reaction tube 11 situating at $S_{17}$ is supplied a carrier 21 such as a synthetic resin particle or glass bead from a carrier supply device 20. It should be noted that the carrier 21 has a diameter smaller than an inner diameter of the large mouth portion 11a of the U-shaped tube 11, but is larger than an inner diameter of the small mouth portion $11b$. On an outer surface of the carrier 21 there has been previously fixed antibody or antigen which causes the antigen-antibody reaction with antigen or antibody substance in the sample to be tested. Further, in the carrier supply device 20, the carriers 21 are wetted with a buffer solution. A reaction liquid in a U-shaped tube 11 at a position $S_{19}$ is sucked into a colorimeter 22, and a carrier 21 contained in a U-shaped tube 11 at a position $S_{20}$ is removed therefrom by means of a carrier discharge device 23. Into a U-shaped tube 11 at a position $S_{22}$ is supplied a washing liquid such as ion exchange water, buffer solution for immunological analysis, physiological saline solution, etc. In a U-shaped tube situated at a position $S_{24}$ is selectively delivered a buffer solution 26 by means of a buffer solution delivery device 25. At positions $S_2$ to $S_5$, a stirring air pump 27 can be detachably connected to small mouth portions $11b$ of U-shaped tubes 11, and at positions $S_{22}$ and $S_{23}$ a discharge pump 28 can be detachably connected to small mouth portions $11b$ of U-shaped tubes 11.

Reaction time periods required for respective test items are respectively set to a sum of a minimum time period and a multiple integer of a basic time period, wherein the minimum time period is assumed to be a rotation period from a reaction start position of the U-shaped tube 11, for example, the sample delivery position $S_1$, to a stop position $S_{22}$ (for instance 15 sec$\times$21), and the basic time period is assumed to be a period during which the U-shaped tube positioned at $S_{22}$ is rotated by one revolution and stopped at $S_{22}$ again (for instance 15 sec$\times$24).

Now, the operation of the automatic analyzer shown in FIG. 3 will be explained also with reference to FIGS. 4A to 4D.

Figure 4A:
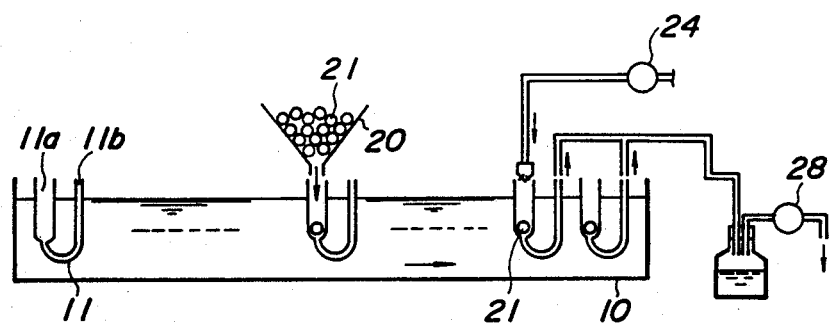
FIGS. 4A to 4D are schematic views showing an operation of the automatic analyzer shown in FIG. 3.

During a first revolution of the turntable 12, at the position $S_{17}$, a carrier 21 wetted with the buffer solution is supplied in a U-shaped tube 11 via its large mouth portion $11a$ as shown in FIG. 4A. Then, at the position $S_{22}$, the washing liquid is intermittently poured into the U-shaped tube 11 through the large mouth portion $11a$ just like a shower by means of the washing pump 24, and at the same time the washing liquid is sucked out of the tube 11 via the small mouth portion $11b$ by means of the discharge pump 28. Next, at the position $S_{23}$, any washing liquid remaining in the tube 11 is discharged by the discharge pump 28. In this manner, the U-shaped reaction tube 11 is washed, and at the same time the buffer solution on the carrier 21 is removed. This ensures that an amount of the buffer solution 26 to be supplied by the buffer solution delivery device 25 can be made to be a given constant value.

Figure 4B:
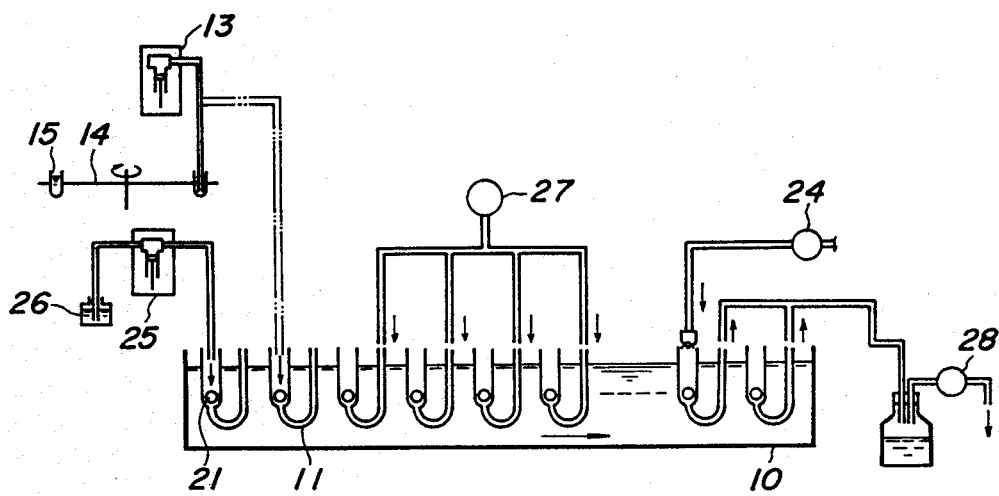

Then, as illustrated in FIG. 4B, at the position $S_{24}$ a given amount of the buffer solution 26 is delivered into the U-shaped tube 11 via its large mouth portion $11a$ by means of the delivery device 25. Then, at the position $S_1$ a given amount of a sample is delivered by means of the sample delivery device 13 into the tube 11 via its large mouth portion $11a$ from a sample cup 15 situated at the sample sucking position of the sampler 14. Next, at the positions $S_2$, $S_3$, $S_4$ and $S_5$, air streams are supplied into the U-shaped tube 11 from its small mouth portion $11b$ by means of the air pump 27 to stir the carrier 21, the buffer solution 26 and sample in the tube 11. In this manner, a first antigen-antibody reaction is effected. It should be noted that the carrier supply device 20, buffer solution delivery device 25, sample delivery device 13 and sampler 14 are made inoperative after being once operated for respective U-shaped tubes.

During a second revolution of the turntable 12, at the position $S_{22}$, the liquid in the tube 11 is sucked via the small mouth portion $11b$ by the discharge pump 28, and at the same time the washing liquid is intermittently poured into the tube 11 via its large mouth portion $11a$ by means of the washing pump 24. The washing liquid remaining in the tube is discharged at the positions $S_{22}$ and $S_{23}$ as shown in FIG. 4B. In this manner, the U-shaped tube 11 and the carrier 21 contained therein are fully washed to effect a first B-F separation.

Heretofore, the explanation was made regarding the case where the reaction time period is at a minimum. If the reaction time period is set to a sum of the minimum time period and a multiple integer of the basic time period, the first B-F separation is effected in the following manner. That is to say, the U-shaped tube 11 into which the sample is delivered at $S_1$ is transported to a position $S_{22}$, and then the U-shaped tube 11 is rotated by the predetermined number of revolutions under the condition that all the devices other than the turntable 12 and the air pump 27 are stopped. After that, the first B-F separation is effected in the manner mentioned above when the tube 11 is moved to the position $S_{22}$.

Figure 4C:
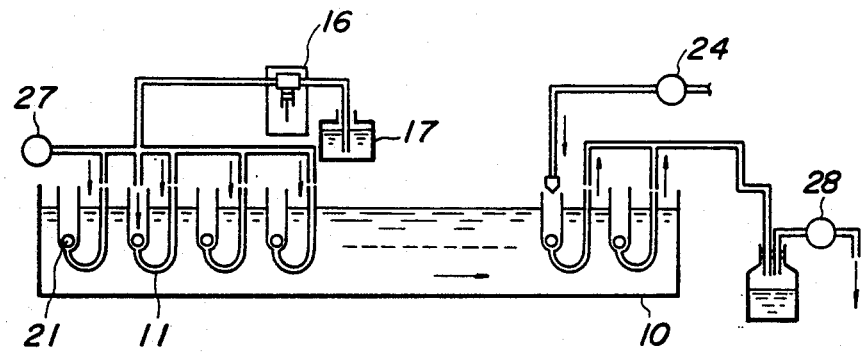

Then, at the position $S_3$ a given amount of the enzyme-labeled reagent 17 is delivered into the U-shaped tube 11 via its large mouth portion $11a$ by the reagent delivery device 16 as illustrated in FIG. 4C. The reagent 17 and carrier 21 are stirred sufficiently at the positions $S_3$, $S_4$ and $S_5$ by supplying the air streams from the small mouth portion $11b$ with the aid of the air pump 27 to effect a second antigen-antibody reaction.

Figure 4D:
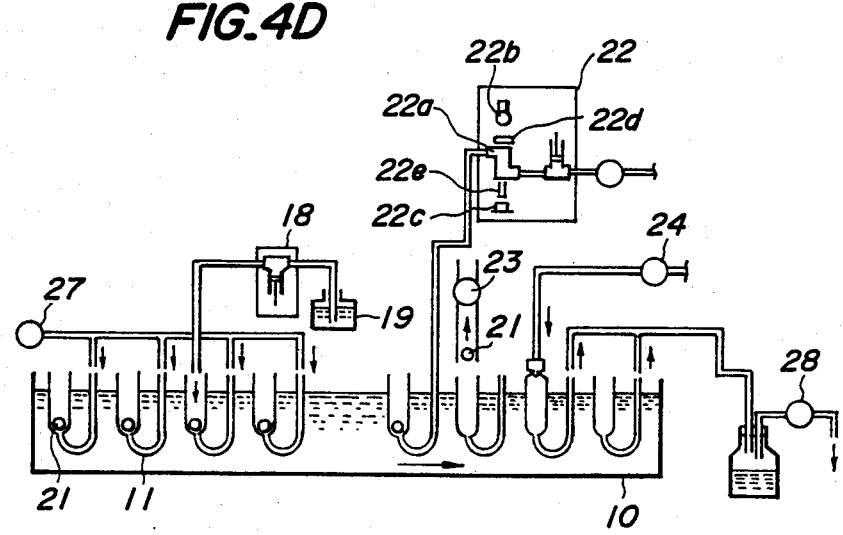

Then, at the positions $S_{22}$ and $S_{23}$ the U-shaped tube 11 and the carrier 21 are washed by means of the washing pump 24 and discharge pump 28 to perform a second B-F separation. In the second antigen-antibody reaction, the reaction time period can be extended from the minimum time period by a multiple integer of the basic time period as in the first antigen-antibody reaction. Next, as shown in FIG. 4D, at the position $S_4$ a given amount of the color reagent 19, i.e. the enzyme substrate reagent, is delivered into the U-shaped tube 11 by the reagent delivery device 18. Then, at the position $S_4$ and $S_5$ the color reagent 19 and the carrier 21 are stirred by means of the air pump 27 to effect a reaction of the color reagent 19 with the labeling enzyme of the enzyme-labeled reagent 17 bound with the carrier 21.

Then, at the position $S_{19}$ a reaction liquid in the U-shaped tube 11 into which the color reagent 19 is delivered is sucked into the colorimeter 22 to effect the colorimetric measurement. As depicted in FIG. 4D, the colorimeter 22 comprises a flow cell $22a$ through which the reaction liquid is caused to flow, and light source $22b$ and detector $22c$ arranged on respective sides of the flow cell $22a$. Light emitted from the light source $22b$ is projected into the flow cell $22a$ via an interference filter $22d$ and light transmitted through the flow cell $22a$ is received by the detector $22c$ by means of a light guide $22e$.

At the position $S_{20}$, the carrier 21 is sucked out of the U-shaped tube 11 via its large mouth portion $11a$ by the carrier discharge device 23. At the position $S_{22}$, the washing liquid is supplied into the U-shaped tube 11 via its large mouth portion $11a$ like a shower, and the washing liquid is sucked out of the tube via its small mouth portion $11b$. The wash liquid remaining in the tube is discharged at the position $S_{23}$. In this manner, the U-shaped tube 11 is prepared for a next supply of a carrier.

Figure 8:
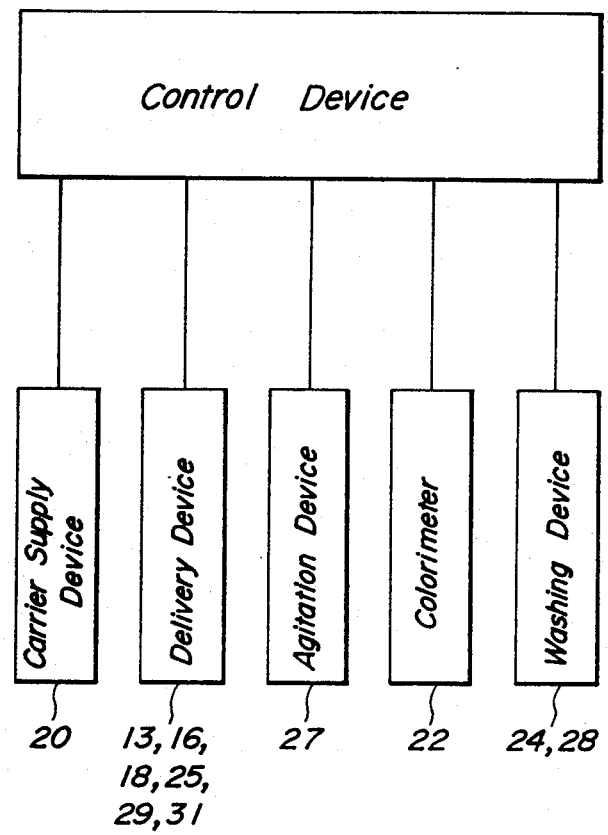
FIG. 8 is a block diagram depicting one embodiment of a control device for controlling the automatic analyzer according to the invention.

As explained above in detail, in the present embodiment use is made of an endless reaction line and only one washing device comprising the washing pump 24 and the discharge pump 28, and the washing operation including the B-F separation is performed. Therefore, the reaction time period can be easily varied at will by controlling on and off operation of the washing device with the aid of a control device shown in FIG. 8.

Figure 5:
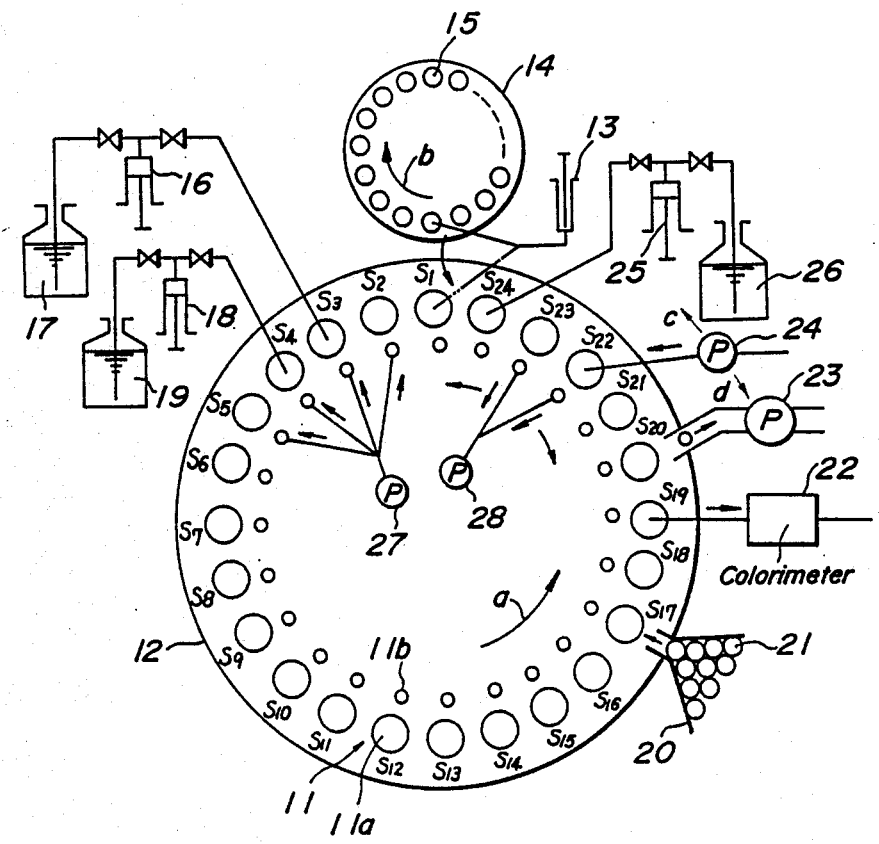
FIGS. 5 and 6 are schematic views showing another embodiment of the enzyme-immuno-assay automatic analyzer according to the invention.

FIG. 5 is a schematic view showing another embodiment of the automatic analyzer for effecting the enzyme-immuno-assay according to the invention. Portions similar to those shown in FIG. 3 are denoted by the same reference numerals used in FIG. 3. In the present embodiment, the washing device arranged in the reaction line, comprising the washing pump 24 and the discharge pump 28, can be moved along the reaction line in arrows c and d directions. Therefore, at first the washing pump 24 and the discharge pump 28 are moved to a position of the U-shaped tube 11 which is determined corresponding to the selected test item, and then the washing operation including the B-F separation is performed in the same manner as mentioned above.

In this case, since the washing device can be moved to any position of the reaction line, the minimum time period of reaction can be determined at will, and therefore a total reaction time period can be set at any desired period suitable for respective test times. Moreover, in the known washing device the time periods for the first and the second antigen-antibody reaction cannot be made equal because the first and second reagent delivery positions are different. However, according to the invention, since the washing device can be moved to a desired position even during the reaction, the time periods for the first and the second antigen-antibody reactions can be made equal, and thus the most suitable reaction time period for respective reactions can be obtained, so that the analyzer can be made simple in construction.

Figure 6:
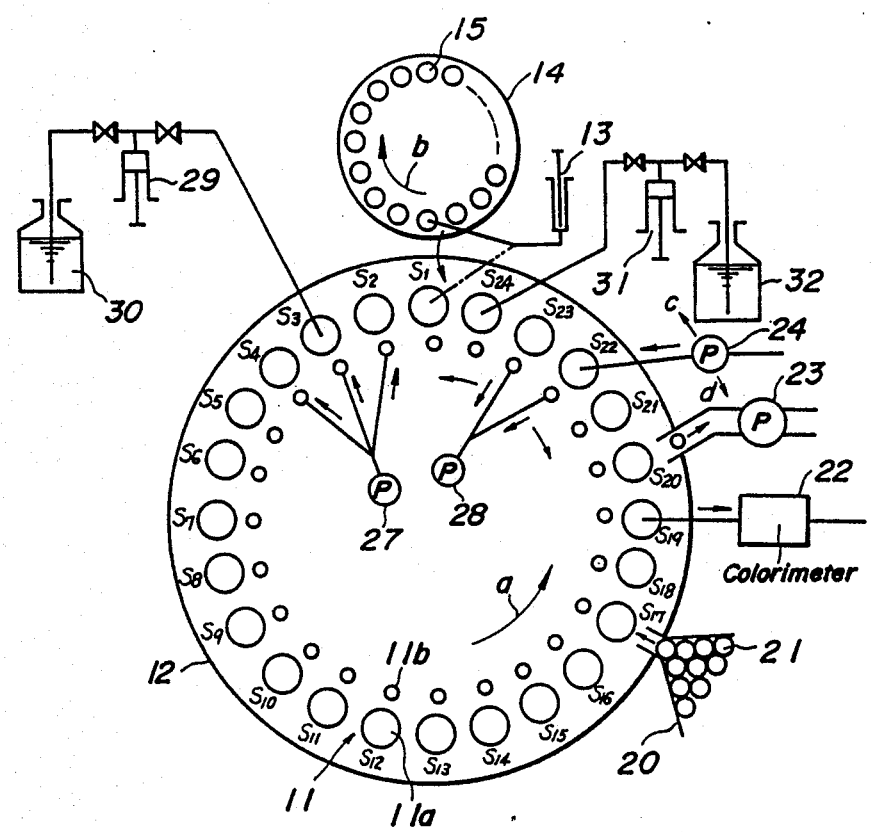

FIG. 6 is a schematic view illustrating an embodiment of the automatic analyzer according to the invention, in which the enzyme-immuno-assay is performed by the competitive method shown in FIG. 1. Also in the present embodiment, portions similar to those shown in FIG. 5 are denoted by the same reference numerals used in FIG. 5. In this embodiment, the delivery of the color reagent at the position $S_4$ and the mixing at the position $S_5$ are removed. At the position $S_3$, a given amount of a color reagent 30 instead of the enzyme-labeled reagent is delivered by means of a reagent delivery device 29, and at the position $S_{24}$ a given amount of an enzyme-labeled reagent 32 instead of the buffer solution is delivered by an enzyme-labeled reagent delivery device 31, said enzyme-labeled reagent 32 being prepared by marking with enzyme same substance as that in a sample to be analyzed. The remaining construction of the analyzer in the present embodiment is entirely the same as that of the embodiment illustrated in FIG. 5.

Now the operation of the enzyme-immuno-assay automatic analyzer illustrated in FIG. 6 will be explained in detail also with reference to FIGS. 7A to 7C.

At first, the washing pump 24 and the discharge pump 28 are moved to a position of the U-shaped tube 11 which is determined corresponding to the selected test item. The washing device comprising the washing pump 24 and the discharge pump 28 can be moved to all the positions $S_1$ to $S_{14}$, but now the washing device is assumed to be positioned at $S_{10}$ for the sake of simplicity of the explanation. At the position $S_{17}$, a carrier 21 wetted with the buffer solution is supplied from the carrier supply device 20 into a U-shaped tube 11 as shown in FIG. 7A. Then, at the position $S_{10}$ the washing liquid is poured intermittently into the tube 11 like a shower by the washing pump 24, and the washing liquid remaining in the tube 11 is sucked out of the tube at the position $S_1$ by means of the discharge pump 28 via the small mouth portion 11b of the U-shaped tube. Next, as illustrated in FIG. 7B, at the position $S_{24}$ a given amount of the enzyme-labeled reagent 32 is delivered into the U-shaped tube 11 from its large mouth portion 11a by means of the reagent delivery device 31, and then at the position $S_1$ a given amount of a sample in a sample cup 15 in the sampler 14 is delivered into the U-shaped tube 11. Next, at the positions $S_2$ to $S_4$ the air streams are caused to flow through the U-shaped tube 11 from its small mouth portion 11b to its large mouth portion 11a with the aid of the air pump 27 to mix the carrier 21, enzyme-labeled reagent 32 and sample with one another to effect the antigen-antibody reaction. It should be noted that the carrier supply device 20, reagent delivery device 31, sample delivery device 13 and sampler 14 are kept inoperative once being operated for respective U-shaped tubes.

After the reaction is started, as shown in FIG. 7B at the position $S_{10}$ the reaction liquid in the U-shaped tube 11 is sucked out of the tube by the discharge pump 28, and at the same time the washing liquid is poured into the tube 11 and the washing liquid remained in the tube 11 is discharged at the positions $S_{10}$ and $S_{11}$ by the pump 28 to effect the B-F separation.

To obtain the desired reaction time period by adding a multiple integer of the basic time period to the minimum time period, the U-shaped tube 1 1 into which the enzyme-labeled reagent 32 and the sample are delivered is transported to a position $S_{10}$, and then the U-shaped tube 11 is rotated by the predetermined number of revolution under the condition that all the devices other than the turntable 12 and the air pump 27 are stopped. After that, the B-F separation is effected in the manner mentioned above when the tube 11 is moved to the position $S_{10}$.

Then, as shown in FIG. 7C at the position $S_3$ a given amount of the color reagent 30 is delivered by the reagent delivery device 29 into the U-shaped tube 11. Next, at the positions $S_3$ and $S_4$ the air streams are passed through the tube 11 with the aid of the air pump 27 to stir the carrier 21 and the color reagent 30 to effect the reaction. Then at the position $S_{19}$ the reacted liquid in the U-shaped tube 11 is sucked into a flow cell of the colorimeter 22 to effect the colorimetric measurement.

In this colorimetric reaction, to obtain the desired reaction time period by adding a multiple integer of the basic time period to the minimum time period the U-shaped tube 11 into which the color reagent 30 is delivered is transported to a position $S_{19}$, and then the U-shaped tube 11 is rotated by the predetermined number of revolutions under the condition that all the devices other than the turntable 12 and the air pump 27 are stopped. After that, the colorimetric measurement is performed by the colorimeter 22 when the tube 11 is moved to the position $S_{19}$ again.

Next, at the position $S_{20}$ the carrier 21 contained in the tube 11 is withdrawn via the large mouth portion 11a by means of the carrier discharge device 23. At the position $S_{10}$, the washing liquid shower is intermittently supplied into the U-shaped tube 11 by the washing pump 24, and at the same time the washing liquid is discharged through the small mouth portion 11b by means of the discharge pump 28. The washing liquid remaining in the tube 11 is discharged at the position $S_{11}$ by the pump 28. In this manner, the U-shaped tube 11 is washed effectively for preparing the analysis of another sample.

In the present embodiment utilizing the competition method, use is made of an endless reaction line and only one washing device arranged movably along the reaction line comprising the washing pump 24 and the discharge pump 28, and the washing operation including the B-F separation is performed. Therefore, the reaction time period can be easily varied at will by controlling on and off operation of the washing device with the aid of the control device shown in FIG. 8. Further, since the washing device can be moved along the reaction line, the minimum time period of the reaction can be variably set.

The present invention is not limited to the embodiments explained above, but many modifications can be conceived within the scope of the invention. In the above embodiments, the enzyme-labeled reagent is used to perform the enzyme-immuno-assay, but the radio-immuno-assay and fluorescent-immuno-assay also may be adopted. Further, it is not necessary to incorporate the circular reaction line, but the reaction line can be formed by a snake chain, Moreover, in the embodiments using the carriers the direct colorimetry may be effected while the test liquid remains in the reaction vessel. In the case, if the carrier affects the measurement it may be withdrawn from the reaction vessel prior to the colorimetry. Further, in this case the carrier discharge may be made simple in construction. Moreover, in the embodiments mentioned above the reaction vessels are used repeatedly, but they may be discharged.

Further, in order to improve the reliability of analysis, the same test item may be measured by two reaction lines. Moreover, in the embodiments shown in FIGS. 3, 5 and 6, the deliveries of the reagents and buffer solution are carried out at different positions, but they may be effected at the same position for example $S_{24}$. Then, the agitation may be performed only at a single position, for instance $S_2$. Further, delivery position, carrier supply position, carrier discharge position, colorimetric measurement position, etc. are not limited to the embodiments mentioned above, but many changes are possible.

Further, in the embodiment mentioned above, the washing device is arranged movably and the minimum time period for the antigen-antibody reaction is varied, but if the colorimeter 22 is arranged movably in a time axis direction of the reaction line the minimum time period for the colorimetric reaction may be varied.

What is claimed is:

1. In a method of automatically analyzing a plurality of different kinds of substances in samples in an immunological manner, comprising transporting in a stepwise manner at a given time period a number of reaction vessels containing carriers onto which given antibody or antigen has been fixed along a plurality of positions of an endless reaction line; delivering samples and labeled reagents into the reaction vessels to initiate antigen-antibody reactions; effecting a B-F separation by separating antigen or antibody bound with the carriers and free antigen or antibody from each other by means of a washing device for washing the reaction vessels; measuring the substances in the samples with the aid of labeling substances of the labeled reagents; and discharging the carriers out of the reaction line; the improvement comprising: controlling said washing device in a manner such that washing is effected when a reaction time period required for said antigen-antibody reaction has elapsed, said reaction time period being set to a sum of a minimum time period and a multiple integer of a basic time period, wherein said minimum time period is equal to a period during which a reaction vessel moves from a reaction start position to a position at which the washing device is provided, and is arbitrarily adjustable within said basic time period by moving said washing device to any position of said endless reaction line, and said basic time period is equal to a period during which a reaction vessel is rotated by one revolution over said endless reaction line, and is adjustable by controlling on and off operation of said washing device at said any position of said endless reaction line.

2. A method according to claim 1, wherein the washing for a sample is effected by means of the same washing device at positions which are arbitrarily adjustable for respective reactions on the reaction line.

3. A method according to claim 1, wherein the reaction vessels are transported along a circular reaction line constituted by a turntable which is rotated intermittently at a constant pitch.

4. A method according to claim 3, wherein the carriers are supplied into the reaction vessels one by one, and, after immunological measurement has been effected and the carriers have been discharged from the reaction vessels, the reaction vessels are washed to prepare for a next analysis.

5. A method according to claim 4, wherein during a first revolution of the turntable after the supply of a carrier into a reaction vessel, a sample is delivered into the reaction vessel to effect a first antigen-antibody reaction for a first reaction time period; during the next revolution of the turntable, when a respective minimum time period has elapsed, the reaction vessel and carrier are washed to effect a first B-F separation, and then an enzyme-labeled reagent is delivered into the reaction vessel to effect a second antigen-antibody reaction for a second reaction time period; during the next revolution of the turntable, when a respective minimum time period has elapsed, the reaction vessel and carrier are washed to effect a second B-F separation; and then a color reagent including enzyme substrate is delivered into the reaction vessel to form a test liquid; and during the next revolution of the turntable, the test liquid is colorimetered, the carrier is discharged and the reaction vessel is washed.

6. A method according to claim 5, wherein after the supply of the carrier into the reaction vessel, but prior to the delivery of the sample into the reaction vessel, the reaction vessel and carrier are washed.

7. A method according to claim 6, wherein prior to the supply of the carrier into the reaction vessel, a buffer solution is poured into the reaction vessel.

8. An automatic analyzer for analyzing a plurality of different kinds of substances in samples in an immunological manner comprising:
   a plurality of reaction vessels;
   an endless reaction line having a plurality of positions;
   means for transporting said reaction vessels along successive positions of said endless reaction line;

a plurality of carriers with antibody or antigen fixed thereto;

means for supplying the carriers with antibody or antigen fixed thereto into reaction vessels;

means for supplying samples into the reaction vessels at a position of said endless reaction line;

means for delivering a labeled reagent into the reaction vessels at a position of said endless reaction line;

means for measuring the substances in the samples with the aid of labeling substances of the labeled reagent;

means for washing the reaction vessels and carriers to effect a B-F separation for separating antigen or antibody bound with the carriers and free antigen or antibody, said washing means being arranged so as to be movable to any position of said endless reaction line;

means for controlling on and off operation of said washing means at said any position of said endless reaction line in accordance with a reaction time period of a current sample to be analyzed; and means for discharging the carriers from the reaction vessels.

9. An analyzer according to claim 8 wherein said sample delivering means comprises a sampler for supporting a number of samples which are successively indexed at a sample sucking position and a delivery device for pouring a given amount of a sample at the sample sucking position into a reaction vessel.

10. An analyzer according to claim 8, wherein said washing means comprises a washing liquid supply pump for supplying a washing liquid into the reaction vessels and a washing liquid discharge pump for sucking the washing liquid out of the reaction vessels.

11. An analyzer according to claim 8, wherein said measuring means comprises a colorimeter having a light source, a detector, a flow cell and a pump for supplying liquids from the reaction vessels to the flow cell.

12. An analyzer according to claim 8, wherein each reaction vessel is formed by a U-shaped tube having large and small mouth portions, and the carriers are supplied into and discharged out of the U-shaped tube via the large mouth portion while the liquids are discharged from the U-shaped tube via the small mouth portion.

13. An analyzer according to claim 12, further comprising means for stirring liquids in the reaction vessels, said stirring means comprising an air pump for causing an air stream to flow through the U-shaped tube via its small mouth portion.

14. An analyzer according to claim 8, wherein said means for transporting the reaction vessels comprises an intermittently rotatable turntable arranged to hold the reaction vessels at a constant pitch to form a circular reaction line.

15. An analyzer according to claim 14, further comprising means for delivering given amounts of a buffer solution into the reaction vessels and means for delivering given amounts of a color reagent into the reaction vessels.

16. An analyzer according to claim 14, further comprising means for stirring liquids in the reaction vessels.

* * * * *